United States Patent [19]

Legendre et al.

[11] 4,283,585

[45] Aug. 11, 1981

[54] HYDROCARBON ISOMERIZATION CATALYSTS AND PROCEDURES FOR THE PREPARATION AND USE THEREOF

[75] Inventors: Michel Legendre; Philippe Engelhard, both of Le Havre, France

[73] Assignee: Compagnie Francaise de Raffinage, Paris, France

[21] Appl. No.: 139,688

[22] Filed: Apr. 14, 1980

Related U.S. Application Data

[60] Division of Ser. No. 936,686, Nov. 27, 1978, Pat. No. 4,201,696, which is a continuation of Ser. No. 713,238, Aug. 10, 1976, abandoned.

[30] Foreign Application Priority Data

Aug. 13, 1975 [FR] France ............................... 75 25224

[51] Int. Cl.³ ........................... C07C 5/22; C07C 5/13
[52] U.S. Cl. ..................... 585/482; 585/742; 585/744; 585/746; 585/747
[58] Field of Search ............... 585/742, 744, 746, 747, 585/482; 252/442, 462, 465

[56] References Cited

U.S. PATENT DOCUMENTS

| | | |
|---|---|---|
| 2,351,577 | 6/1944 | Thomas ............................. 585/744 |
| 2,733,219 | 1/1956 | Bloch ............................... 585/744 |
| 2,900,425 | 8/1959 | Bloch et al. ...................... 585/744 |
| 3,523,912 | 8/1970 | Jaffe ................................. 252/442 |
| 3,632,525 | 1/1972 | Rausch ............................. 252/442 |
| 3,649,704 | 3/1972 | Hayes ............................... 252/442 |
| 3,923,915 | 12/1975 | Franek et al. .................... 585/744 |
| 3,939,102 | 2/1976 | Hayes ............................... 252/442 |
| 3,948,762 | 4/1976 | Hayes ............................... 252/442 |

FOREIGN PATENT DOCUMENTS

| | | | |
|---|---|---|---|
| 2087685 | 12/1971 | France ............................ 252/465 |
| 2,187,885 | 1/1974 | France ............................ 252/462 |
| 2,187,886 | 1/1974 | France ............................ 252/462 |
| 2,242,147 | 3/1975 | France ............................ 252/442 |
| 1374863 | 11/1974 | United Kingdom .............. 252/442 |

*Primary Examiner*—Curtis R. Davis
*Attorney, Agent, or Firm*—Curtis, Morris & Safford

[57] ABSTRACT

Hydrocarbon isomerization catalysts comprising typically refractory mineral oxide carrier such as alumina and a halogen element present in combined form, together with, in the free or combined state:

A platinum-group metal;
second element from the group consisting of titanium, zirconium, tungsten and molybdenum; and
a metal halide such as $AlCl_3$.

8 Claims, 1 Drawing Figure

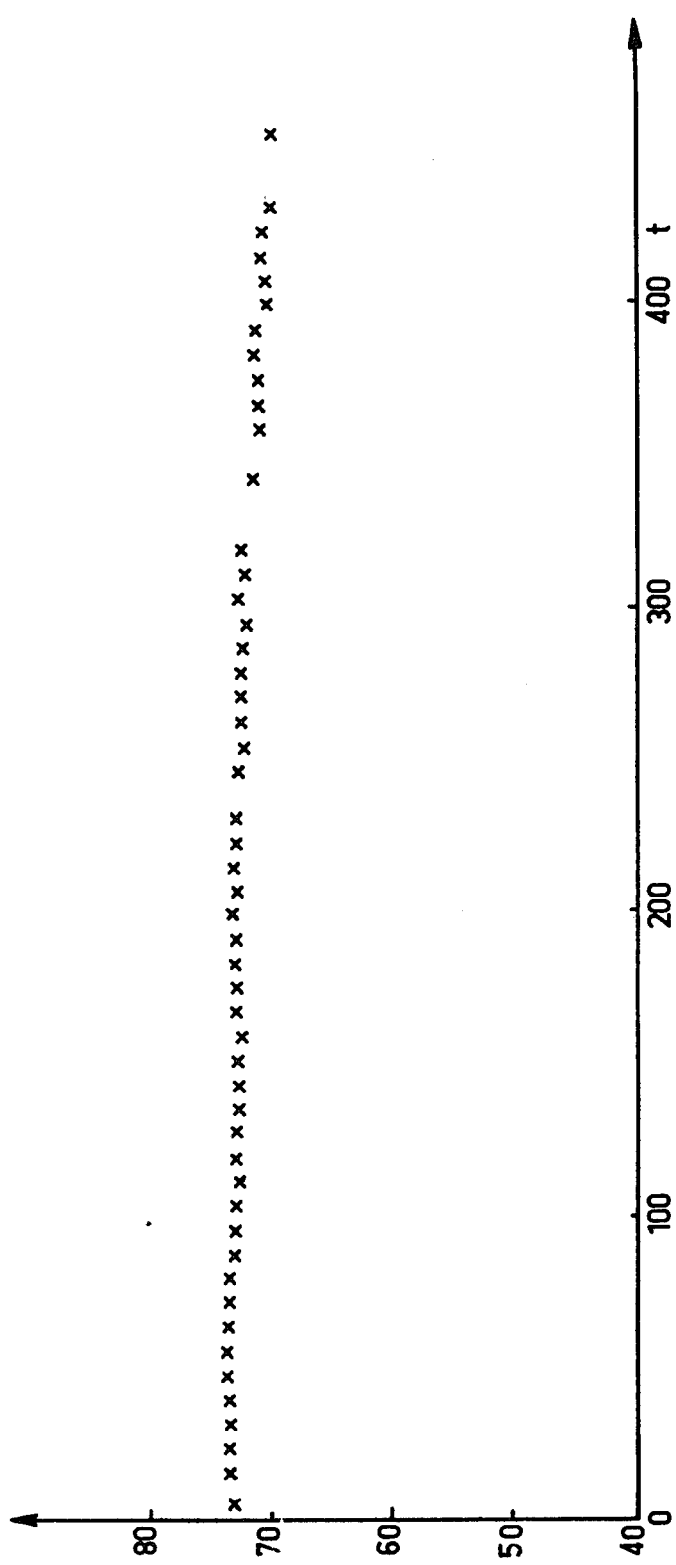

HYDROCARBON ISOMERIZATION CATALYSTS AND PROCEDURES FOR THE PREPARATION AND USE THEREOF

This is a division of application Ser. No. 936,686, filed Nov. 7, 1978, now U.S. Pat. No. 4,201,696, which is a continuation of application Ser. No. 713,238, filed Aug. 10, 1976, and now abandoned.

The present invention relates to new catalysts for the isomerization of hydrocarbons, and particularly of normal paraffins, a process for the preparation of said catalysts, and the application thereof to the isomerization of hydrocarbons.

Many isomerization catalysts of varying compositions have already been proposed. These catalysts generally are formed by a carrier, which may be an alumina, an aluminosilicate, or a mixture of the two. Among the known isomerization catalysts there are those comprising a noble metal, and particularly platinum, with which may be associated tin, nickel, germanium, rhenium, lead and certain metals of groups Ib, IIb, Vb, VIIb, III and IV of the periodic table of the elements, and comprising further a metal halide such as aluminum trichloride.

The applicants have developed new catalysts having satisfactory catalytic properties in their application to the isomerization of hydrocarbons.

The present invention thus has as its object to provide new catalysts for the isomerization of hydrocarbons which have good activity and good selectivity.

The invention consequently has as a first embodiment, catalysts for the isomerization of hydrocarbons comprising a carrier formed at least in part by at least one refractory mineral oxide, and comprising a halogen element present in combined form, said catalysts being characterized by the fact that they comprise and/or consist essentially of, in the free or combined state:

At least one platinum-group metal, and preferably platinum;

at least one second element selected from the group consisting of titanium, zirconium, molybdenum and tungsten; and at least one metal halide.

In this definition of the invention, and throughout the present application, "platinum-group metal" means one of the following metals: Ruthenium, rhodium, palladium, osmium, iridium and platinum.

A second embodiment of the present invention is a process for the preparation of catalysts in accordance with the invention, said process being characterized by the fact that it involves the following steps:

At least one impregnation with at least one solution containing at least one element selected from the group consisting of titanium, zirconium, molybdenum, tungsten and the platinum-group metals, and an aftertreatment with a metal halide employing means known in the art.

A third embodiment of the present invention is a process for the isomerization of hydrocarbons characterized by the fact that said hydrocarbons are contacted, under conditions known in the art, with hydrogen and at least one of the catalysts in accordance with the invention.

The carriers of the catalysts in accordance with the invention should be refractory materials having sufficient specific surface and specific pore volume and having, moreover, acid sites. The specific surface may be comprised between 15 and 350 m$^2$ per gram, and preferably between 100 and 350 m$^2$ per gram, the specific pore volume being greater than 0.1 cm$^3$ per gram. These materials (often referred to as a refractory mineral oxide, or more commonly as a refractory metal oxide) may, for example, be alumina, silica, an aluminosilicate, magnesia, zirconia, the oxides of gallium, titanium, thorium or boron, or a mixture of these oxides.

The most advantageous catalysts are those whose platinum-group metal content is comprised between 0.02 and 2%, based on the weight of the carrier. To obtain satisfactory catalytic properties, said content is preferably held above 0.10%; however, for reasons of catalyst cost, it is preferably limited to 0.75%. The weight percentage given herein are referred to the elemental form.

The content of metal or metals selected from the group consisting of titanium, zirconium, molybdenum and tungsten is comprised between 0.005 and 8%, based on the weight of the carrier, since below 0.005% no improvement is observed over a catalyst containing only platinum, and above 8% the increase in content does not entail a significant increase in activity. Moreover, the applicants have found that the most efficacious contents are those comprised between 0.01 and 3%.

The total halogen content may be comprised between 0.1 and 15%, and preferably between 0.5 and 7%, based on the total catalyst weight.

The process for preparation of the catalysts in accordance with the invention involves a first step consisting of the deposition of the metals on the carrier by known means, for example, by impregnation with solutions containing said metals, either as anions or cations. They may be deposited in any order and the titanium, zirconium, molybdenum, tungsten and platinum-group metals may be deposited simultaneously or successively. However, the applicants have found that it is preferable to deposit the platinum-group metal or metals last with the last impregnating solution.

The acidity of the carrier may be altered in the course of the various impregnations, particularly by means of a treatment with an acid solution, for example, a solution of hydrochloric acid. The activity of the acid sites present on the carrier may thus be increased.

After the deposition of the metals, the carrier may be dried, then calcined at a temperature which in the case of the metals other than the platinum-group metals is comprised between 400° and 700° C., and preferably between 500° and 650° C., and in the case of the platinum-group metals is under 600° C. In the case of platinum, it is preferably less than 550° C.

At the conclusion of the deposition of the metals on the carrier, the halogen content of the solid obtained is comprised between 0.1 and 2%, based on the weight of the carrier. The halogen, preferably chlorine, is combined with the elements forming the carrier and/or with the elements deposited on the carrier at the end of the impregnation treatment. In the remainder of this specification, it will be referred to as the "combined halogen."

The deposition of the metals on the carrier is followed by a treatment with a metal halide from the group consisting of aluminum trichloride, aluminum tribromide, ferric chloride or bromide, beryllium or zirconium chloride, or any mixture of these halides. However, the applicants prefer to use aluminum trichloride.

Before the treatment with the metal halide is carried out, it is, however, preferable to adjust the "combined halogen" content of the solid to be treated. This adjustment of the "combined halogen" content may be effected, for example, by treating said solid with a gaseous mixture of steam and halogen compound, which may be diluted in another gas or mixture of gases such as air, particularly at a temperature comprised between 400° and 700° C. and on the order of 500° C., for example. If the halogen is chlorine, a steam-hydrogen chloride mixture, for example, may be used. After this gas treatment, the solid may be dried at between 80° and 320° C., then calcined at between 370° and 600° C. for a time which may vary but should be less than 10 hr. and should preferably be comprised between 1 and 5 hr.

It is then necessary to treat the solid with an anhydrous gas, that is to say, a gas containing less than 20 ppm of water by volume, just before the metal halide is deposited. Good results are obtained by passing a stream of hydrogen substantially free from water over the solid at a temperature comprised between 400° and 700° C., and preferably between 400° and 600° C., for a time of about 1 to 10 hr.

Before the metal halide treatment, the solid so obtained contains slightly more "combined halogen" than after the deposition of the metals on the carrier. For example, if the solid initially contained from 0.1 to 2% by weight of the composition of "combined halogen", the solid obtained may contain from about 0.8 to 2.5% of "combined halogen" after the halogen-content adjusting step.

The metal halide treatment may be effected by any suitable means known in the art. For example, aluminum trichloride may be sublimed on the product at a temperature comprised between about 190° and 700° C., and preferably between 200° and 600° C., under atmospheric or higher pressure, in the presence of diluent gases such as hydrogen, inert gases, or light paraffinic hydrocarbons. The impregnation may be effected discontinuously but it is preferable to proceed by passing sublimed aluminum trichloride vapors in admixture with a gas such as hydrogen over the catalyst. The halide then becomes fixed on the solid previously obtained. However, to eliminate the unreacted halide, the catalyst must be brought to a temperature above 300° C. and scavenged with an inert gas such as nitrogen. The duration and temperature of this latter treatment depend on the excess of unfixed metal halide that remains on the catalyst. Generally, a temperature of from 400° to 700° C. and preferably comprised between 500° and 600° C., and a duration of from 1 to 48 hr. will suffice to eliminate this excess. The catalyst ultimately obtained in this last step contains from 0.1 to 15%, and preferably from 0.5 to 7%, of total halogen, based on the total weight of the catalyst, the preferred halogen being chlorine. "Total halogen" means both the "combined halogen" defined earlier and the halogen resulting from the metal halide treatment.

The catalysts in accordance with the invention are intended to be used in a process for the izomerization of hydrocarbons, and more particularly of paraffinic hydrocarbons. The conditions of temperature and pressure are known in the art. Thus, the temperature is comprised between 20° and 450° C., the pressure between 1 and 100 atmospheres (hydrogen pressure), the molar ratio of hydrogen to hydrocarbons (introduced into the reactor) ranging from 0.5 to 20, and the space velocity, measured in the liquid state and based on the volume of charge passing over a unit volume of catalyst in one hour (vol./vol./hr.), being comprised between 0.1 and 10. A wide range of hydrocarbon charges may be treated. Besides xylenes, olefins and other charges, the applicants have found that the catalysts in accordance with the invention are very well suited to the isomerization of paraffinic hydrocarbons.

In fact, the catalysts ultimately obtained have proved more advantageous than a conventional catalyst containing only platinum and a metal halide deposited on a refractory mineral oxide carrier, as will be shown by the example which follows, which is in no wise limitative and is given only by way of illustration.

In this example, the charge consists of normal pentane, the hydrocarbon generally used to test isomerization catalysts; but it might also consist of the hydrocarbons mentioned earlier.

EXAMPLE 1

This example relates to the preparation and utilization of six catalysts in accordance with the invention. There will be described successively the preparation of six catalysts A1, A2, B1, B2, C and D as well as that of two control catalysts T1 and T2, then their application to the hydro-isomerization of normal pentane.

Preparation of Catalysts

The refractory carrier used with all of the catalysts described below is an alumina whose characteristics are as follows:

| | |
|---|---|
| Specific surface: | 190 m$^2$/g |
| Pore volume: | 0.51 cm$^3$/g |
| Average pore radius: | 53 A |
| Chlorine content (measured by x-ray fluorescence): | 0.4% by weight of the alumina |
| Form: | Extrudator with an average diameter of 1.5 mm |

This alumina, calcined for 4 hr. at 600° C. before the deposition of the various metals, will hereinafter be called the "carrier alumina."

Preparation of Control Catalysts T1 and T2

The carrier alumina is immersed in a dilute hydrochloric acid solution of a normality of about 0.1 N. After dewatering at ambient temperature, the alumina is contacted with a circulating solution of hexachloroplatinic acid whose initial platinum concentration is such that the catalyst contains about 0.35% by weight of platinum. After dewatering followed by drying at 120° C., the solid is calcined at about 530° C. in a muffle kiln.

The solid is then subjected to a treatment for adjustment of its chlorine content. To this end, a gaseous stream of steam and hydrogen chloride is passed over it at a temperature of 500° C. for 4 hr. The solid obtained is then calcined for 1 hr. at the same temperature.

Finally, the solid is subjected to a reduction with hydrogen for about 1 hr. at 500° C. It contains 1.36% chlorine and 0.33% platinum.

In order to obtain the two control catalysts, the solid is then divided into two portions, which are then separately subjected to the aluminum chloride treatment.

13 grams of each portion is scavenged with a stream of sublimed aluminum trichloride and hydrogen (total pressure of gas stream, 1 atmosphere; partial pressure of aluminum trichloride, 30 torr).

For the first portion, which will form the catalyst T1, this treatment is effected for 2½ hr. at 300° C.

For the second portion, which will form the catalyst T2, this treatment is effected for 2½ hr. at 500° C.

The two portions are then treated with a stream of anhydrous nitrogen at about 500° C. for elimination of the unreacted aluminum trichloride.

Thus the two controls T1 and T2 are obtained. Their characteristics are presented in Table 2.

Preparation of Catalysts A1, A2, B1, B2, C and D 100 g of carrier alumina is impregnated with 250 cm³ of a solution containing 20 cm³ of hydrochloric acid RP and a certain weight of a compound of titanium, molybdenum, zirzonium or tungsten, depending on the catalyst to be prepared. The weights and compounds are given in Table 1 below.

TABLE 1

| Catalyst | Compound Used | Weight of Compound (grams) |
|---|---|---|
| A1 | $Ti_2(C_2O_4)_3 \cdot 10H_2O$ | 0.8962 |
| A2 | $Ti_2(C_2O_4)_3 \cdot 10H_2O$ | 2.3315 |
| B1 | $ZrO(NO_3)_3 \cdot 2H_2O$ | 0.327 |
| B2 | $ZrO(NO_3)_3 \cdot 2H_2O$ | 0.980 |
| C | $(NH_4)_6Mo_7O_{24} \cdot 4H_2O$ | 0.184 |
| D | $(NH_4)_{10}W_{12}O_{41} \cdot 7H_2O$ | 0.4438 |

After evaporation in a rotary evaporator, the catalyst is dried at about 120° C., then calcined for 2 hr. at 600° C.

There are then effected an acidification of the carrier, an impregnation with a hexachloroplatinic acid solution, an adjustment of the chlorine content and a reduction with hydrogen which are identical in all respects with the operations described earlier for control catalysts T1 and T2.

The solids obtained are then subjected to an aluminum trichloride treatment identical with the one effected on T1 for 2½ hr. at 300° C.

The compositions of the catalysts T1, T2, A1, A2, B1, B2, C and D are presented in Table 2 below.

TABLE 2

| Catalyst | Composition in wt. % in solid before $AlCl_3$ treatment | | | | Final chlorine content of catalyst, wt. % |
|---|---|---|---|---|---|
| | Pt | Other Metal | Per cent of other metal | Cl | |
| T1 | 0.33 | | | 1.36 | 5.85 |
| T2 | 0.33 | | | 1.36 | 4.68 |
| A2 | 0.36 | Ti | 0.22 | 1.45 | 5.88 |
| A2 | 0.35 | Ti | 0.60 | 1.22 | 5.48 |
| B1 | 0.38 | Zr | 0.23 | 1.30 | 5.58 |
| B2 | 0.38 | Zr | 0.46 | 1.16 | 5.19 |
| C | 0.36 | Mo | 0.14 | 1.35 | 5.38 |
| D | 0.36 | W | 0.26 | 1.23 | 5.81 |

Catalytic Tests

Catalytic tests are then performed on each of these catalysts in the following manner: Normal pentane and hydrogen are passed, at a pressure of 30 bars and a temperature of 150° C., over 10 cm³ of catalyst placed in a reactor. The space velocity, defined earlier, is 3, and the molar ratio of $H_2$ to hydrocarbon is 2.5.

The only reaction product is isopentane. The activity of the various catalysts may therefore be evaluated on the basis of the conversion of the normal pentane. The results are reported in Table 3 for each catalyst.

TABLE 3

| Catalyst | Conversion of normal pentane, % |
|---|---|
| T1 | 43 |
| T2 | 40 |
| A1 | 55 |
| A2 | 54 |
| B1 | 62 |
| B2 | 62 |
| C | 60 |
| D | 48 |

From these results, it is apparent that the catalysts in accordance with the invention possess good activity for isomerization. In fact, the catalysts in accordance with the invention exhibit considerably greater activity than the control catalysts containing only platinum.

EXAMPLE 2

With a view to verifying the good behavior with time (stability) of the catalytic formulations in accordance with the invention, a catalytic test comparable to that described in Example 1 was run on the following catalyst:

Carrier: An alumina identical with that of Example 1:

| Pt | 0.35% |
|---|---|
| Zr | 0.33% |
| Cl | 3.81% |

The charge was normal pentane to which 100 ppm of chlorine in the form of 1-2-dichloropropane had been added. The volume of catalyst in the reactor here was 25 cm³, the space velocity was 5, and the molar ratio of hydrogen to normal pentane was 3.

The graph in the drawing shows the evolution of the ispentane yield of the reaction. The graph shows the percentage of isopentane formed in the isomerization reaction extended for more than 400 hours. This yield is defined as the ratio of number of molecules of isopentane to number of molecules having five carbon atoms.

As may be seen, the catalyst is very stable with time. Moreover, an analysis of the catalyst at the end of the test showed that it contained only 0.13% carbon, which is very little.

We claim:
1. A process for the isomerization of hydrocarbons comprising contacting said hydrocarbons under conditions favoring isomerization with hydrogen and a catalyst consisting essentially of a carrier which is comprised of at least one refractory metal oxide, including a halogen element present in combined form, and deposited on said carrier:
   from about 0.02 to 2 wt. %, based on the weight of the carrier, of at least one platinum-group metal;
   from about 0.005 to 8 wt. %, based on the weight of the carrier, of at least one second element from the group consisting of titanium, zirconium, tungsten and molybdenum; and
   at least one metal halide based on the weight of the carrier, selected from the group consisting of aluminum trichloride, aluminum tribromide, ferric chloride, ferric bromide, beryllium dichloride, zirconium chloride and mixtures thereof, the total halogen content of said catalyst being 0.1 to 15 wt. % of the total weight of the catalyst, wherein at least one of said platinum group metal and at least one second element are introduced onto the carrier by impregnation and thereafter at least one metal halide is introduced onto the carrier by sublimation.

2. In the process of claim 1, the further improvement wherein the process for the preparation of said catalyst comprises the following steps:

at least one impregnation of the carrier with at least one solution containing at least one element from the group consisting of titanium, zirconium, molybdenum, tungsten and the platinum-group metals, at least one of the impregnating solutions comprising either cations of the elements titanium, zirconium, molybdenum and tungsten, or anions containing said elements, and an aftertreatment with at least one metal halide selected from the group consisting of aluminum trichloride, aluminum tribromide, ferric chloride, ferric bromide, beryllium dichloride and zirconium chloride.

3. A process for the isomerization of hydrocarbons comprising contacting said hydrocarbons under conditions favoring isomerization with hydrogen and a catalyst consisting essentially of a carrier which is comprised of at least one refractory metal oxide, including chlorine present in combined form, and deposited on said carrier:

from about 0.10 to 0.75 wt. %, based on the weight of the carrier, of platinum;

a second element of zirconium;

a metal halide of aluminum trichloride, and wherein at least one of said platinum group metal and at least one second element are introduced onto the carrier by impregnation and thereafter at least one metal halide is introduced onto the carrier by sublimation wherein the percentages of said platinum, said second element, and said chlorine are respectively 0.10 to 0.75 wt. %, 0.01 to 3 wt. % and 0.5 to 7 wt. %, and wherein said carrier is an alumina having a specific surface comprised between 100 and 350 $m^2/g$, and a specific pore volume greater than 0.1 $cm^3/g$, and said carrier has acid sites.

4. A process for the isomerization of hydrocarbons comprising contacting said hydrocarbons under conditions favoring isomerization with hydrogen and a catalyst, the improvement wherein said catalyst consists essentially of a carrier comprised of at least one refractory metal oxide, including a halogen element present in combined form in an amount from 0.1 to 2.5 wt. %, and the following deposited on said carrier:

from 0.02 to 2 wt. % of platinum;

from 0.005 to 8 wt. % of zirconium; and said percentages being based on the elemental form relative to the weight of the carrier;

the total halogen content of said catalyst being 0.1 to 15 wt. % of the total weight of the catalyst; and said process comprises the following steps:

at least one impregnation of the carrier with at least one solution containing at least one element from the group consisting of titanium, zirconium, molybdenum, tungsten and the platinum-group metals, at least one of the impregnating solutions comprising either cations of the elements titanium, zirconium, molybdenum and tungsten, or anions containing said elements, and an aftertreatment with at least one metal halide selected from the group consisting of aluminum trichloride, aluminum tribromide, ferric chloride, ferric bromide, beryllium dichloride and zirconium chloride, and wherein at least one of said platinum group metal and at least one second element are introduced onto the carrier by impregnation and thereafter at least one metal halide is introduced onto the carrier by sublimation.

5. A process according to one of claims 1 to 3 or 4, wherein the hydrocarbons subjected to isomerization are paraffinic hydrocarbons.

6. A process according to one of claims 1 to 3 or 4, wherein the isomerization conditions comprise a temperature of between 200° and 450° C., a hydrogen pressure of between 1 and 100 atmospheres, a molar ratio of hydrogen to hydrocarbons of from 0.5 to 20, and a space velocity measured in the liquid state of between 0.1 and 10 volumes of charge per volume of catalyst per hour.

7. A process according to claim 6, wherein the hydrocarbons subjected to isomerization are paraffinic hydrocarbons.

8. A process according to claim 6, wherein the hydrocarbons subjected to isomerization comprise xylenes or olefins.

* * * * *